US007521531B2

(12) United States Patent
Govindan

(10) Patent No.: US 7,521,531 B2
(45) Date of Patent: Apr. 21, 2009

(54) METHODS FOR THE PURIFICATION OF STABLE RADIOIODINE CONJUGATES

(75) Inventor: Serengulam V. Govindan, Summit, NJ (US)

(73) Assignee: Immunomedics, Inc., Morris Plains, NJ (US)

( * ) Notice: Subject to any disclaimer, the term of this patent is extended or adjusted under 35 U.S.C. 154(b) by 289 days.

(21) Appl. No.: 10/359,276

(22) Filed: Feb. 6, 2003

(65) Prior Publication Data
US 2003/0220470 A1 Nov. 27, 2003

(51) Int. Cl.
*A61K 38/00* (2006.01)
*A61K 38/04* (2006.01)
(52) U.S. Cl. .......................... 530/345; 514/2; 424/1.69
(58) Field of Classification Search ................. 530/345
See application file for complete search history.

(56) References Cited

U.S. PATENT DOCUMENTS

| 5,246,840 | A | * | 9/1993 | Nilsson ..................... 435/101 |
| 5,273,738 | A | | 12/1993 | Matthews et al. |
| 5,274,076 | A | | 12/1993 | Barbet et al. |
| 5,554,745 | A | | 9/1996 | Chiu et al. |
| 6,663,866 | B1 | | 12/2003 | Govindan |
| 6,818,742 | B1 | | 11/2004 | Govindan |
| 6,858,705 | B2 | | 2/2005 | Govindan et al. |
| 7,147,856 | B2 | | 12/2006 | Govindan |
| 2003/0235534 | A1 | * | 12/2003 | Griffiths et al. ............ 424/1.49 |

FOREIGN PATENT DOCUMENTS

| EP | 0 492 478 B1 | 7/1995 |
| EP | 0 419 387 B1 | 11/1996 |
| GB | 2 109 407 A | 6/1983 |
| JP | 03173900 | 7/1991 |
| WO | WO 95/29707 | 11/1995 |
| WO | WO 9616677 | 6/1996 |
| WO | WO 98/08548 | 3/1998 |
| WO | WO 99/11294 | 3/1999 |

OTHER PUBLICATIONS

Protein Purification. http://en.wikipedia.org/wiki/Protein purification.*
Ion Exchange Chromatography. http://en.wikipedia.org/wiki/Ion_exchange_chromatography.*
http://www-nmr.cabm.rutgers.edu/academics/biochem694/reading/ProteinPurification_Vermont.pdf.*
Bianchi, C. P., *Chemical Abstracts, 1-Pharmacology* (1988) 1:404-405.
Deys et al., "Comparative Targeting of Human Colon-Carcinoma Multicell Spheroids Using One- and Two-step (Bispecific Antibody) Techniques," *Chemical Abstracts* (1996) 125(23):883-891.
Dumas, P. et al., "Specifité de L'iodotyrosine Desiodase des Microsomes Thyroidiens et Hepatiques," *Biochimica et Biophysica Acta* (1973) 293:36-47.
Franano, F. N. et al., "Metabolism of Receptor Targeted $^{111}$In-DTPA-Glycoproteins: Identification of $^{111}$In-DTPA-ϵ-lysine as the Primary Metabolic and Excretory Product," *Nucl Med. Biol* (1994) 21(8):1023-1034.
Goldenberg, D. M., "Monoclonal Antibodies in Cancer Detection and Therapy," *The American Journal of Medicine*, (Mar. 1993) 94:297-312.
Govindan et al., "Labeling of Monoclonal Antibodies with Diethyltriaminepentaacetic Acid-Appended Radioiodinated Peptides Containing D-Amino Acids," *Bioconjugate Chemistry*, 1999, 10:231-240.
Govindan, S. V., et al., "Thiolations, $^{99m}$Tc Labelings, and Animal n Vivo *Biodistributions of Divalent Monoclonal Antibody Fragments*," *Bioconjugate Chem.* (1996) 7:290-297.
Hansen, H. J. et al., "Characterization of Second-Generation Monoclonal Antibodies Against Carcinoembryonic Antigen," *Cancer* (Jun. 1993) 71(11):3478-3485.
Pawlak-Byczkowska, E. J. et al., "Two New Monoclonal Antibodies, EPB-1 and EPB-2, Reactive with Human Lymphoma," *Cancer Research* (Aug. 1989) 49:4568-4577.
Seham, A. A. et al., "Improving the Tumor Retention of Radioiodinated Antibody: Aryl Carbohydrate Adducts," *Cancer Research* (Suppl.) (Feb. 1990) 50:783-788.
Stein, R. et al., "Effects of Radiolabeling Monoclonal Antibodies with a Residualizing Iodine Radiolabel on the Accretion of Radioisotope in Tumors," *Cancer Research* (Jul. 1995) 55:3132-3139.

(Continued)

*Primary Examiner*—Andrew D. Kosar
*Assistant Examiner*—Maury Audet
(74) *Attorney, Agent, or Firm*—Richard A. Nakashima

(57) ABSTRACT

The present invention is directed toward a method for preparing and purifying a conjugate of a radioiodinated aminopolycarboxylate-appended peptide and a targeting agent. The method involves (A) providing a solution comp rising (i) unbound radioiodine (ii) a radioiodinated aminopolycarboxylate-appended peptide that is not conjugated to a targeting agent (iii) and a radioiodinated aminopolycarboxylate-appended peptide that is conjugated to the targeting agent; (B) contacting the solution with an anion-exchange resin; and (C) passing the anion-exchange resin and solution together through a filter capable of trapping anion-exchange resin particles.

23 Claims, 3 Drawing Sheets

OTHER PUBLICATIONS

Stein, R. et al., "Murine Monoclonal Antibodies Raised Against Human Non-Small Cell Carcinoma of the Lung: Specificity and Tumor Targeting," *Cancer Research* (Feb. 1990) 50:1330-1336.

Strobei, J. L. et al., "I-Glycoconjugate Labels for Identifying Sites of Protein Catabolism in Vivo: Effect of Structure and chemistry of Coupling to Protein on Label Entrapment in Cells after Protein Degradation," *Archives of Biochemistry and Biophysics*, (Aug. 1985) 240(2):635-645.

Wilbur, D. S. et al., "Development of a Stable Radioiodinating Reagent to Label Monoclonal Antibodies for Radiotherapy of Cancer," *Journal of Nuclear Medicine* (1989) 30:216-226.

Lee, H. et al., "Development of a Kit-Form Analog of Metaiodobenzylguanidine", The Journal of Nuclear Medicine, vol. 27, pp. 256-267 (1986).

Stein, R., et al., "Improved Iodine Radiolabels for Monoclonal Antibody Therapy", Cancer Research, vol. 63, pp. 111-118 (2003).

Weadock, K.S., et al., "Evaluation of a Remote Radioiodination System for Radioimmunotherapy", The Journal of Nuclear Medicine, vol. 31, No. 4, pp. 508-510 (1990).

Reist, Craig J., et al., "Radioiodination of Internalizing Monoclonal Antibodies Using N-Succinimidyl 5-Iodo-3-Pyridinecarboxylate," Cancer Research 56, 4970-4977, Nov. 1, 1996.

Foulon, Catherine F., et al., "Radioiodination via D-Amino Acid Peptide Enhances Cellular Retention and tumor Xenograft Targeting of an Internalizing Anti-Epidermal Growth Factor Receptor Variant III Monoclonal Antibody" Cancer Research 60, 4453-4460, Aug. 15, 2000.

Shankar, Sriram, et al., "N-Succinimidyl 3-[131]Iodo-4-phosphonomethylbenzoate ([131]SIPMB), a Negatively Charged Substituent-Bearing Acylaation Agent for the Radioiodination of Peptides and mAbs" Bioconjugate Chem. 2003, 14, 331-341.

Sharkey, Robert M., et al., "Advantage of Residualizing Radiolabels for an Internalizing Antibody Against the B-cell Lymphoma Antigen, CD22" Cancer Immunol Immunother (1997) 44: 179-188.

Shih, Lisa, et al., "Localization of an antibody to CD74 (MHC class II invariant chain) to human B cell lymphoma Xenografts in nude mice" Cancer Immunol Immunother (2000) 49:208-216 XP-002202222.

Shih, Lisa B., et al., "The Processing and Fate of Antibodies and Their Radiolabels Bound to the Surface of Tumor Cells in Vitro: A comparison of Nine Radiolabels" The journal of Nuclear Medicine, vol. 35, No. 5, May 1994.

Ali, Seham, et al., "Synthesis and Radioiodination of Tyramine cellobiose for Labeling Monoclonal Antibodies," Nucl. Med. Biol., vol. 15, No. 5, pp. 557-561, 1988.

Stein, Rhona, et al., "Targeting Human Cancer Xenografts with Monoclonal Antibodies Labeled Using Radioiodinated, Diethylenetriaminepentaacetic Acid-appended peptides" Clinical Cancer Research, vol. 5, 3079s-3087s, Oct. 1999 (Suppl.).

Pearson, Randall K., et al., "Establishment of a New Short, Protease-Resistant, Affinity Labeling Reagent for the cholecystokinin receptor" Biochemical and Biophysical Research Communications, vol. 147, No. 1, 1987, pp. 346-353.

Thorpe, Suzanne R., et al., "The design and application of residualizing Labels for Studies of Protein and Catabolism" The FASEB Journal, vol. 7, Mar. 1993.

Ali, Seham A., et al., "Improving the Tumor Retention of Radioiodinated Antibody: Aryl Carbohydrate Adducts" Cancer Research (Suppl.), 50, Feb. 1, 1990, pp. 783s-788s.

* cited by examiner

METHODS FOR THE PURIFICATION OF STABLE RADIOIODINE CONJUGATES

RELATED APPLICATIONS

This application is a continuation-in-part of application Ser. No. 09/696,740, filed Oct. 26, 2000, which is a continuation-in-part of application Ser. No. 09/605,873, filed Jun. 29, 2000, which is a continuation-in-part of application Ser. No. 08/919,477, filed Aug. 28, 1997, and claims priority to PCT/US97/23711, filed Dec. 19, 1997, and PCT/US97/14998, filed Aug. 27, 1997; and benefit of Provisional Application No. 60/024,783, filed Aug. 28, 1996. The content of these applications in their entirety is incorporated by reference.

FIELD OF THE INVENTION

This invention relates to the purification of reagents used in radioimmunodetection and radioimmunotherapy and specifically to the purification of radioiodine labeled conjugates having enhanced stability in vivo and enhanced retention at tumor sites.

BACKGROUND OF THE INVENTION

Radioiodinated monoclonal antibodies are important for the diagnosis and therapy of cancer as summarized by Goldenberg in Amer. J. Med. 1993; 94: 297-312. A number of methods have been developed over the last thirty years to chemically introduce radioiodine into monoclonal and polyclonal antibodies for these uses. Iodine is preferred as a radiolabel in these applications because the chemistry used for radioiodination of protein is relatively easy, radioiodine has useful physical decay characteristics, and isotopes of iodine are commercially available. Various chemistries have been developed to link iodine to antibodies that target cancer cells. These chemistries have been reviewed by Wilbur, Bioconjugate Chemistry 1992; 3: 433-70. The most common linking procedure has been to prepare in situ an electrophilic radioiodine species to react with a functional group on an antibody. Reagents such as chloramine-T and iodogen have been employed to generate electrophilic iodine. A tyrosine group on protein is usually the site of iodination.

Conventional radioiodinations of MAbs require the removal of oxidant used as well as unincorporated radioiodide using some purification method. When using buffer-soluble oxidant such as chloramine-T, the oxidant and radioiodide are customarily removed by size-exclusion chromatography on a size-exclusion column, such as commercially available PD10® column.

A major drawback with using the direct radioiodination schemes is the phenomenon of in vivo deiodination. As a result of antibody internalization and lysosomal processing in vivo, a labeled protein is degraded to small peptides, and its radioiodine is released from the cell in the form of iodotyrosine or as iodine attached to a low molecular weight peptide fragment. These findings have been reported by Geissler et al., Cancer Research 1992; 52: 2907-2915 and Shih et al., J. Nucl. Med. 1994; 35: 899-908. Such in vivo removal of radioiodine from target cells reduces tumor-to-nontumor discrimination which is important for radiodiagnosis, and also reduces the residence time of radioiodine in target cells which significantly affects radiotherapy effectiveness.

Several approaches have been devised to overcome the phenomenon of in vivo deiodination, through the design of iodine radiolabels which are intracellularly retained. Such labels are referred to as "residualizing labels". In one method, radioiodine is attached to non-metabolizable carbohydrates, and the latter are first activated and then conjugated to antibodies. This approach is exemplified by lactitoltyramine (LT) and dilactitoltyramine (Strobel et al., Arch. Biochem. Biophys 1985; 240: 635-45) and tyrosine cellobiose (Ali et al., Cancer Research 1990; 50: 783s-88s). In another approach, a pyridine-based moiety, "SIPC", was utilized (Reist et al., Cancer Research 1996; 56:4970-4977). Pentapeptides containing all D amino acids and multiple basic amino acids, have also been explored (Foulon et al., Cancer Research 2000; 60:4453-4460). In yet another approach, DTPA-appended, radioiodinated peptides containing D-amino acids were successfully utilized as residualizing labels (Govindan et al., Bioconjugate Chemistry 1999; 10:231-240; Stein et al., Cancer Research 2003; 63:111-118).

When a radioiodinated small molecular mass material is conjugated to MAbs (hereinafter radioiodinated conjugates), as illustrated in the references given in the previous paragraph, an additional requirement presents itself in that the unconjugated material needs to be removed as well. This invariably requires an additional column method of purification. The carbohydrate method results in low overall yield and specific activity, and involves a column method of purification at the end of the process. The methods of Reist et al (supra) and Foulon et al (supra) involve two column purification steps, one at the radioiodination stage and the other at the antibody conjugation stage. The method of Govindan et al. (supra; further described in Stein et al. (supra)) involves one column purification at the end of the process, with higher overall yields and specific activities.

Column methods are generally cumbersome, and have additional drawbacks of radiation exposure to personnel, especially when handling hundreds of mCi of I-131 for clinical-scale preparations, and catastrophic column failures. In iodogen-based radioiodinations, the oxidant is water-insolube, and is removed by simply syringing out or filtering off the radiolabeled material. In these instances, the only other material that needs to be removed is unincorporated radioiodide. Because of the relatively higher affinity of iodide versus phosphate or hydroxide ion to bind to strong anion-exchange resin, unincorporated iodide has been shown to be removable by using an anion-exchange resin [Weadock et al. J Nuclear Medicine 1990; 31:508-511); Behr™ et al. Nuklearmedizin 2002; 41:71-79). It is also conceivable to use immobilized chloramine-T oxidant such as commercially available "IODO-BEADS"® in combination with anion exchange resin. While a certain simplification is achieved in the purification of directly radioiodinated antibodies by such combinations, the use of radioiodinated conjugates still requires the removal of unconjugated small molecular mass moieties. In as much as this purification is usually achieved by column methods, the attendant drawbacks of the methods pose practical problems in the purification of several hundreds of millicuries of radiolabeled preparations for clinical applications.

A column method has been described by Li et al. (Bioconjugate Chemistry 1994; 5: 101-104) to purify a radiometal-chelated DOTA-peptide from unlabeled DOTA-peptide by passing through a column of diethylaminoethyl-cellulose anion-exchanger, and eluting with several portions of water. In this case, radiometal-chelated DOTA peptide has a neutral charge, and is therefore eluted from the column, while unlabeled material, with negative charge on the chelator portion, is retained by the anion-exchange column. This was necessitated by the need to purify radiometal-chelated bifunctional material, which was subsequently conjugated to antibodies, and the product was purified by size-exclusion column method. Thus, the procedure of Li et al. (supra) involves a multi-step approach and two column-based purification steps. Again, such column-based methods will be impractical when applied to large-scale radioiodination of small molecular mass moieties followed by conjugation to targeting agents. In the latter case, involving hundreds of millicuries of radioactive iodine, simpler purification methods are necessitated.

SUMMARY OF THE INVENTION

The present invention solves the above-identified problems by providing purification methods for radioiodinated conjugates which are prepared by covalent linking of radioiodinated aminopolycarboxylate-appended peptides to targeting agents.

The present invention addresses the need for a purification system for a radioiodinated conjugate derived from the various radioiodinated, aminopolycarboxylate-appended, moieties and targeting agents. In contrast to the methods previously known in the art, pertaining to direct radioiodination of targeting agents such as antibodies, the present invention relates a procedure involving the radioiodination of a low molecular mass entity, such as a tyrosine-containing bifunctional peptide, and conjugating the radioiodinated moiety to antibodies. As such, the present invention addresses the need to remove by purification both unincorporated radioiodide and unconjugated radioiodinated moiety.

Methods of the invention provide greater efficiencies of antibody labeling with residualizing iodine labels. The methods also provide higher quality stable radioiodine conjugate preparations having a low aggregate content. Other advantages, such as the simplification and safe-handling entailed in a one-pot preparation and purification method, will become apparent from the following detailed description.

DEFINITIONS

Figure 1:
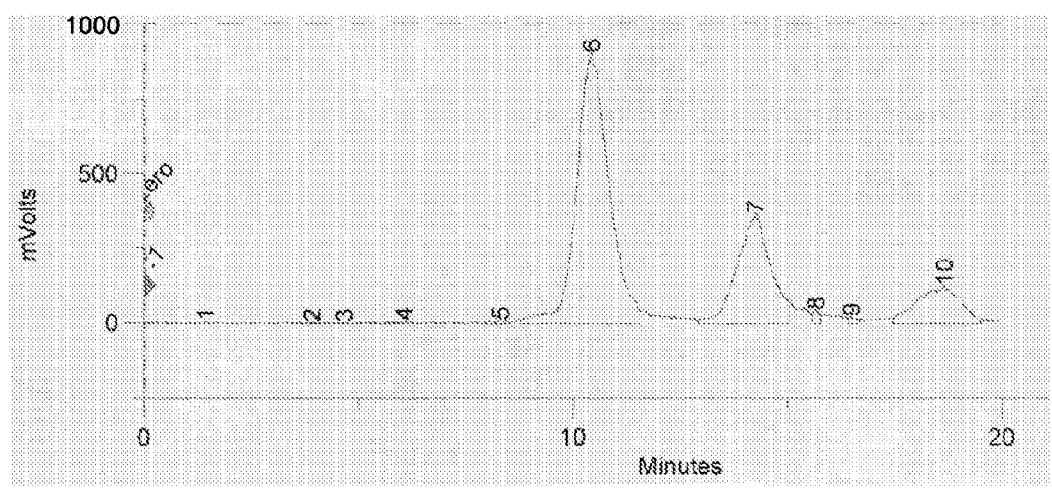
FIG. 1 shows the size-exclusion (SEC) HPLC of crude (unpurified) product (I-131-IMP-R4-hMN-14). The main peak~10 min retention is due to labeled hMN-14, while peaks near 14 min and 18 min represent unconjugated I-131-IMPR4 and I-131 respectively.
Figure 2:
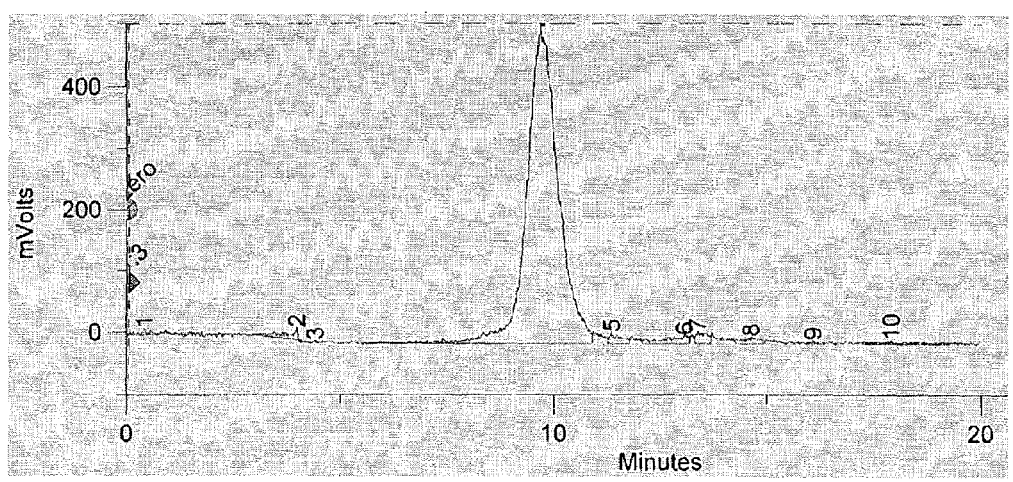
FIG. 2 shows the SEC HPLC of purified I-131-IMPR4-hMN14 and demonstrates that unconjugated I-131-IMPR4 and I-131 are completely removed by anion exchange.
Figure 3:
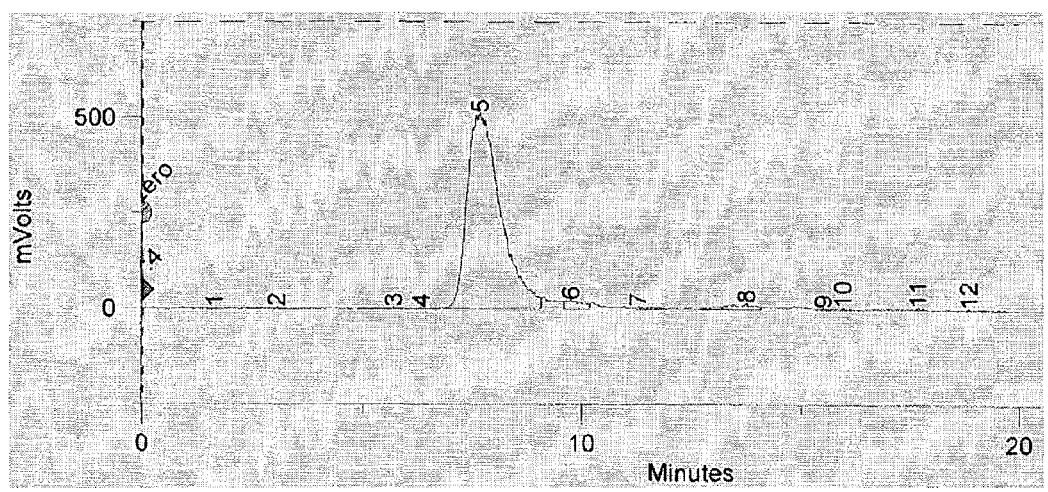
FIG. 3 shows that the SEC-HPLC of a mixture of purified product and the antigen carcinoembryonic antigen (CEA) complexation, and this HPLC shows that the immunoreactivity of the product is completely maintained as illustrated by the complete shift of the peak due to labeled antibody to that of the higher MW material of antibody-antigen complex.

In the description that follows, a number of terms are utilized extensively. Definitions are provided here to facilitate understanding of the invention.

Targeting agent. A "targeting agent" is a molecular moiety capable of selectively binding to a target cell. Examples of a targeting agent include a protein molecule, which can target an antigen or a receptor expressed by tumor or infectious lesion, or a low molecular mass moiety which can target a specific receptor on a tumor or a lesion, or synthetic nucleotides targeted to tumor cells or lesions. Preferred targeting agents include, antibodies and peptides.

Antibody. The term "antibody" includes monoclonal antibodies, such as marine, chimeric, humanized or human antibodies, as well as antigen-binding fragments. Such fragments include Fab, Fab', F(ab)2, and F(ab')2, which lack the Fc fragment of an intact antibody. Such fragments also include isolated fragments of the light chain variable region "Fv" fragments of the variable regions of the heavy and light chains, (sFv)2 fragments (see, for example: Tai et al., Cancer Research Supplement, 55:5983-5989, 1995), and recombinant single chain polypeptide molecules in which light and heavy variable regions are connected by a peptide linker. By "multivalent" antibody it is meant that the antibody may bind more than one antigen, which may have the same or a different structure, simultaneously. By "multispecific" antibody it is meant that the subject antibody may bind simultaneously to at least two antigens which are of different structure.

Conjugate. As used herein, a conjugate is a molecule comprising an unlabeled or a radiolabeled aminopolycarboxylate-appended peptide (also referred to as "low molecular mass moiety"), which is covalently linked to a targeting agent such as a monoclonal antibody. The conjugate retains the biospecificity of the targeting agent. For example, the immunoreactivity (ability to bind antigen) of the antibody targeting agent is roughly the same, or only slightly reduced, after conjugation compared to that before conjugation with the low molecular mass moiety.

Aminopolycarboxylate-appended peptide. The term "aminopolycarboxylate-appended peptide" refers to the chemical moieties formed by the covalent linking of an aminopolycarboxylic acid to a peptide. The linking preferably via the amino groups of the peptide. Any suitable aminopolycarboxylate is contemplated for use with this invention. Exemplary aminopolycarboxylates include iminodiacetic acid, nitrilotriacetic acid, EDTA (ethylenediaminetetraacetic acid), DTPA (diethylenetriaminetetraacetic acid), TTHA (triethylenetetraminehexaacetic acid), DOTA (1,4,7,10-tetraazacyclododecane N,N',N'',N'''-tetraacetic acid), or various backbone-substituted versions thereof, such as, for example, isothiocyanatobenzyl-EDTA/DTPA/TTHA/DOTA, among numerous other aminopolycarboxylates and their derivatives which can be readily envisaged. The term peptide is defined below.

Peptide. The use of the term "peptide" in the phrase aminopolycarboxylate-appended peptide refers to any peptide assembled from L or D-amino acids, or a combination of both L and D-amino acids. The peptide is preferably assembled from 2-40 amino acids, more preferably 2-5 amino acids, and most preferably 3-4 amino acids. Optimally, the peptide has at least one D-tyrosine which is liked to a basic amino acid such as L or D-lysine, with the latter constituting the carboxy terminus of the peptide. This basic amino acid can be bound to the aminopolycarboxylic acid.

Solution. As used herein, solution refers to the solution containing the conjugate of antibody and radioiodinated aminopolycarboxylate, unincorporated radioiodide and unincorporated radioiodinated aminopolycarboxylate. A preferred solution is a buffered aqueous solution.

Unbound radioiodine. As used herein, unbound radioiodine refers to radioactive iodine species that is not oxidized to reactive iodine species, and includes unoxidized radioiodide, which is not bound to the peptide.

Anion-exchange resin. As used herein, "anion-exchange resin" refers to commercially available insoluble synthetic or natural polymer matrices containing either protonated tertiary amine or tetraalkylammonium functional groups, wherein the counterions (anions) are exchangeable with anions of test substrates.

Filter. As used herein, "filter" refers to any device which can retain particulate matter, such as filter size between 0.10 μm and 0.30 μm, more preferably a filter with about 0.22 μm pore diameter size.

Oxidant. As used herein, "oxidant" refers to any oxidizing agent which is used to oxidize radioiode to active radioiodo monochloride molecule, which is the radioiodinating species in radioiodination reactions, as discussed in Wilbur (supra).

Iodogen method. This term refers to radioiodination procedure involving the use of iodogen as oxidant. Iodogen (1,3,4,6-tetrachloro-3☐,6☐-diphenylglycoluril) is a water-insoluble material which generates active radioiodinating species upon contact with a solution of radioiodide, as discussed in Wilbur (supra).

Chloramine-T method. This term refers to the use of chloramine-T (sodium N-chlorotoluenesulfonamide) as a water-soluble oxidant which generates active radioiodinating species upon mixing with a solution of radioiodide, as discussed in Wilbur (supra).

Linking moiety. A linking moiety is a functional group capable of forming a covalent bond to the targeting agent, selected from the group comprising maleimide, chloroacetamide, bromoacetamide, iodoacetamide, vinylsulfone, N-hydroxysuccinimide ester, N-hydroxysulfosuccinimide ester, amidate ester, isocyanate, or isothiocyanate. The linking moiety is introduced into aminopolycarboxylate-appended peptide using homobifunctional or heterobifunctional cross-linking molecules. The use of homobifunctional and heterobifunctional reagents as cross-linkers is well known in the art (Wong, S. S., 1991; Chemistry of protein conjugation and cross-linking; CRC Press, Boca Raton, Fla.; pp 1-48).

DETAILED DESCRIPTION OF THE INVENTION

Surprisingly, the inventors have found that brief contact with an anion-exchange resin efficiently removes unconjugated low molecular mass moieties. The purified product is isolated by filtration from the anion-exchange resin. For the filtering of the resin from the conjugate, and the unreacted iodide and the iodinated aminopolycarboxylate-appended peptide removed by the resin, any filtering device that can trap the particulate matter is applicable. A 0.22 μm filter device is most preferred. The method of removing unconjugated low molecular mass material by stirring with anion-exchange resin works particularly well with the aminopolycarboxylate moieties of the present invention, such as DTPA.

The efficient removal of unconjugated polycarboxylate moieties, by a simple one-pot purification, which avoids cumbersome column method of purification, has been unexpectedly discovered. Based on the selectivity of counterions for anion exchange resin, one would not be able to predict that a short duration of contact with anion exchange resins could efficiently remove unconjugated low molecular mass moieties, such as polycarboxylates. For example, hydroxide is considered to have weak binding abilities to anion exchange resin, and an acetate group binds only marginally better than hydroxide. An acetate group relates to the present aminopolycarboxylates in that aminopolycarboxylates contain acetic acid residues on nitrogen atoms, and these acetic acid residues are ionized fully as acetates in buffer solutions with pH>6. For example, based on manufacturer's product literature (AG® 1 and AG 2 Strong Anion Exchange Resin Instruction Manual, BioRad Corporation) the selectivity of iodide is 175-fold that of hydroxide (which is arbitrarily taken as 1) on AG 1® anion-exchange resin, while that of acetate is only 3.2-fold better than that of hydroxide. Moreover, the resin is used in phosphate form which has a relative selectivity of 5 (compared to 1 for hydroxide), which is slightly higher than that of acetate. The relatively higher selectivity of iodide for binding to anion exchange resin only predicts successful removal of the iodide by an ion-exchange procedure. However, despite the lower selectivity of acetate versus phosphate ion to bind to anion exchange resin, the inventor has found that the ion-exchange method works efficiently in removing the unconjugated small molecular material containing aminopolycarboxylates, which could not be predicted based on anion-exchange resin binding selectivity. While not wishing to be bound by any theory, the inventor believes that this improved selectivity is due to the presence of multiple acetate groups in the same molecule, as depicted by the aminopolycarboxylate sub-structure of the small molecular mass moiety. Thus, it has been discovered that, by incorporating aminopolycarboxylate moieties in the small molecular mass material, unconjugated-radioiodinated material can be efficiently removed by simply stirring for a few minutes with a suspension of anion-exchange resin, and filtering off the product. The simplified procedure of the instant invention is operationally distinct, and advantageous, over the method of Li et al. (supra) in that the column method of purification is completely avoided.

Anion Exchange Resin

For these experiments, commercially available strongly basic anion-exchange resin, containing quaternary ammonium groups attached to styrene divinylbenzene copolymer lattice, was used. This resin had a 8% cross-linkage corresponding to the pore size with MW exclusion limit of 1000 Da, and a medium mesh size of 100-200 (150-75 μm particle diameter).

However, the invention is not limited to the specific anion-exchange resin characteristics mentioned above, but includes both strongly basic anion-exchange resin, described above, and weakly basic anion-exchange resin, such as commercially available diethylaminoethyl cellulose. In addition, the extent of cross-linkage on the resin used is not limiting. In the specific instance of the strongly basic anionic resin, the cross-linkage can vary from 2% (pore size with MW exclusion limit of 2700 Da) to 12% (pore size with MW exclusion limit of 400 Da), and the particle size of the resin can be in the range of 20 mesh-400 mesh, corresponding to 850 μm-38 μm particle diameter range.

Conjugates

The present invention pertains to the use of nonmetabolizable and radioiodinated peptides which are used for labeling antibodies so that the radioactivity is residualized in vivo. These specially designed peptides contain 2-to-40 amino acids, preferably 2-to-5 amino acids, and preferably contain D-amino acids. D-amino acids are preferably used at the peptide between the site of attachment of the peptide to an antibody and a radioactive iodine that is bound to a tyrosine or tyramine. Most preferably, within this region, there no two adjacent amino acids that are L-amino acids. Glycine in this context is an L-amino acid. By using D-amino acids in this way, the peptide bonds that connects the radioactive iodine to the antibody cannot be hydrolyzed in the lysosome. In addition, one or more aminopolycarboxylate moieties are appended to the peptide, and the N-terminus and/or a side chain amino group are linked to a cross-linker possessing a functional group for covalent binding to an antibody. The covalently antibody-binding group can be an amino residue (for site-specific attachments to oxidized Fc portion carbohydrate of MAbs), an imidate or isothiocyanate (attachable to lysine groups of proteins), maleimide, bromo- or iodoacetamide residue (specific to thiols on MAbs) and the like. The amino acid(s) immediately following the last D-tyrosine unit, and which are used to introduce antibody-binding cross-linkers, can be natural L-amino acids. The aminopolycarboxylate unit can be iminodiacetic acid, nitrilotriacetic acid, EDTA (ethylenediaminetetraacetic acid), DTPA (diethylenetriaminetetraacetic acid), TTHA (triethylenetetraminehexaacetic acid), DOTA (1,4,7,10-tetraazacyclododecane N,N',N'',N'''-tetraacetic acid), NOTA (1,4,7-triazacyclononane-N,N',N''-triacetic acid) or various backbone-substituted versions thereof, such as, for example, 1-[(p-isothiocyanato)benzyl]-EDTA (benzyl-EDTA), 1-[(p-isothiocyanato)benzyl]-DTPA (benzyl-DTPA), 1-[(p-isothiocyanato)benzyl]-TTHA (benzyl-TTHA), 1-[(p-isothiocyanato)benzyl]-DOTA (benzyl-DOTA), 1-[(p-isothiocyanato)benzyl]-NOTA (benzyl-NOTA), among numerous other aminopolycarboxylates and their derivatives which can be readily envisaged.

In another embodiment, the bifunctional iodinatable aminopolycarboxylate is derived by attaching a tyramine group and an antibody-binding group to the aminopolycarboxylate. No protease-susceptible bond is involved in these structures. Alternatively, aminopoly-carboxylates, backbone-substituted with an antibody-binding unit, are converted to corresponding dianhydrides which are then reacted with D-tyrosine to obtain an entity that contains two D-tyrosine residues. Since the amide bond(s) between the bifunctional aminopolycarboxylate and D-tyrosine will not be recognized by proteases, these constitute a different version of residualizing iodine labels.

The fact that iodinated D-tyrosine moiety will be resistant toward deiodinases is an advantageous property that can be used with the present invention. This possibility is described by Dumas et al., Biochem. Biophys. Acta 1973; 293:36-47.

Examples of aminopolycarboxylate-appended peptide useful for radioiodinating an antibody selected from the group consisting of: X-Gly-D-Tyr-D-Lys ((1-(p-CSNH)benzyl)DTPA)-OH; X-D-Ala-D-Tyr-D-Tyr-D-Lys(DTPA); [X-D-Ala-D-Tyr-D-Tyr-D-Lys(½DTPA)]2; X-Lys(X)-Lys ((1-(p-CSNH)benzyl)DTPA)-D-Tyr-D-Tyr-D-Lys((1-(p-NH)benzyl)DTPA)-OH; X-Lys(X)-Lys((1-(p-CSNH)benzyl)DTPA)-D-Tyr-D-Lys((1-(p-CSNH)benzyl)DTPA)-OH; X-Asp-D-Tyr-D-Lys((1-(p-CSNH)benzyl)DTPA)-OH; X-Lys(X)-Asp-D-Tyr-D-Lys((1-(p-CSNH)benzyl)DTPA)-OH; X-Asp-D-Tyr-D-Lys((1-(p-CSNH)benzyl)DTPA)-OH; and X-Lys(X)-Asp-D-Tyr-D-Lys((1-(p-CSNH)benzyl) DTPA)-OH; wherein X is a cross-linker containing a functional group for covalent linking to targeting vectors, including proteins such as monoclonal antibodies, fragments and constructs thereof.

Examples of suitable within the scope of the invention, the radioiodine is I-123, I-124, I-125 or I-131.

Antibodies

In a preferred embodiment of the present invention, antibodies, such as MAbs, multivalent antibodies and multi specific antibodies, are used that recognize or bind to markers or tumor associated antigens that are expressed at high levels on target cells and that are expressed predominantly or only on diseased cells versus normal tissues, as well as antigens associated with certain normal cells and tissues that are to be ablated, such as bone marrow cells and ectopic tissues, such as parathyroid, spleen and endometrium, and antibodies that internalize rapidly. By "multivalent" antibody it is meant that the antibody may bind more than one antigen, which may have the same or a different structure, simultaneously. By "multispecific" antibody it is meant that the subject antibody may bind simultaneously to at least two antigens which are of different structure. For example, an antibody having two different specificities would be considered multivalent and multispecific because it can bind two structurally different targets simultaneously. On the other hand, an antibody having two or more specific arms which bind the same target, but no other specificities, would be multivalent but not multispecific. A variety of multispecific and/or multivalent antibodies can be produced using molecular engineering. For example, a bispecific fusion protein can be monovalent, consisting of, for example, a scFv with a single binding site for one antigen and a Fab fragment with a single binding site for a second antigen. A bispecific antibody can also be divalent, consisting of, for example, an IgG with two binding sites for one antigen and two scFv with two binding sites for a second antigen.

Antibodies useful within the scope of the present invention include mAbs with properties as described above, and contemplate the use of, but are not limited to, the following mAbs: LL1 (anti-CD74), LL2 (anti-CD22), RS7 (anti-epithelial glycoprotein-1 (EGP-1)), PAM-4 (anti-MUC1), MN-14 (anti-carcinoembryonic antigen), Mu-9 (anti-colon-specific antigen-p), AFP (anti-alpha-fetoprotein), antiprostate specific membrane antigen (PSMA), such as J591, and G250 (anti-carbonic anhydrase IX). Other useful antigens that may be targeted using these conjugates include HER-2/neu, CD19, CD20, VEGF, EGF receptor, alkaline phosphatase, prostatic acid phosphatase, tenascin, placental growth factor (PlGF), insulin-like growth factor (ILGF), and gangliosides.

In another preferred embodiment of the present invention, antibodies are used that internalize rapidly and are then re-expressed, processed and presented on cell surfaces, enabling continual uptake and accretion of circulating immunoconjugate by the cell. An example of a most-preferred antibody/antigen pair is LL1 an anti-CD74 mAb (invariant chain, class II-specific chaperone, Ii). The CD74 antigen is highly expressed on B cell lymphomas, certain T cell lymphomas, melanomas and certain other cancers (Ong et al., Immunology 1999; 98:296-302).

The diseases that are treated with anti-CD74 antibodies, for example, include, but are not limited to, non-Hodgkin's lymphoma, melanoma and multiple myeloma. Continual expression of the CD74 antigen for short periods of time on the surface of target cells, followed by internalization of the antigen, and re-expression of the antigen, enables the targeting LL1 antibody to be internalized along with any therapeutic moiety it carries as a "payload." This allows a high, and therapeutic, concentration of LL1-therapeutic immunoconjugate to be accumulated inside such cells. Internalized LL1 immunoconjugates are cycled through lysosomes and endosomes, and the residualizing radioactive moiety is thus retained within the target cells.

In a preferred embodiment the antibodies that are used in the treatment of human disease are human or humanized (cdr-grafted) versions of antibodies; although murine and chimeric versions of antibodies can be used. For veterinary uses, the same-species IgG would likely be the most effective vector, although cross-species IgGs would remain useful. Same species IgG molecules as delivery agents are mostly preferred to minimize immune responses. This is particularly important when considering repeat treatments. For humans, a human or humanized IgG antibody is less likely to generate an anti-IgG immune response from patients. Targeting an internalizing antigen, antibodies such as hLL1 and hLL2 rapidly internalize after binding to target cells, which means that the radioiodinated antibody conjugate being carried is rapidly internalized into cells.

The MAb is murine, chimeric, humanized, or human antibodies, and can be intact, fragments or various engineered versions thereof. In a particularly preferable embodiment, the MAb is derivatized or disulfide-reduced to possess thiol groups.

Antibody Targets

Antibodies can be used against various diseased tissues, cells, and organisms, such as cardiovascular lesions (e.g., clots, emboli, atherosclerotic plaques), amyloid deposits (e.g., amyloidosis and in Alzheimer's disease), infectious organisms (e.g., bacteria, fungi, rickettsia, viruses, parasites), inflammation (e.g., Class III autoimmune diseases such as immune-mediated thrombocytopenias, such as acute idiopathic thrombocytopenic purpura and chronic idiopathic thrombocytopenic purpura, dermatomyositis, Sjogren's syndrome, multiple sclerosis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, post-streptococcal nephritis, erythema nodosum, Takayasu's arteritis, Addison's disease, rheumatoid arthritis, sarcoidosis, ulcerative colitis, erythema multiforme, IgA nephropathy, polyarteritis nodosa, ankylosing spondylitis, Goodpasture's syndrome, thromboangitis ubiterans, Sjogren's syndrome, primary biliary cirrhosis, Hashimoto's thyroiditis, thyrotoxicosis, scleroderma, chronic active hepatitis, polymyositis/dermatomyositis, polychondritis, pamphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis and fibrosing alveolitis, etc.), displaced or ectopic normal tissues (e.g., parathyroid, endometrium, spleen, thymus), and cancers (liquid (e.g., leukemias and lymphomas) and solid (e.g., carcinomas, sarcomas, gliomas, melanomas).

The present invention is illustrated with examples below without limiting the scope thereof.

EXAMPLES

Example 1

Simplified One-Pot Preparation and Purification Method for Labeling Disulfide-Reduced Anti-CEA MAb, hMN-14, with Radioiodinated IMP-R4

The procedure is illustrated below using IMP-R4 as the small molecular mass material which is radioiodinated and conjugated to disulfide-reduced anti-CEA MAb, hMN-14. IMP-R4 has the structure MCC-Lys(MCC)-Lys((1-(p-CSNH)benzyl)DTPA)-D-Tyr-D-Lys((1-(p-CSNH)benzyl) DTPA)-OH, wherein MCC is 4-(N-maleimidomethyl)-cyclohexane-1-carbonyl. IMP-R4 is part of the subject of U.S. patent application Ser. No. 09/696,740, filed Oct. 26, 2000.

I-131 sodium iodide from the supplier was buffered with 7-times its volume of 0.5 M sodium phosphate pH 7.4, and transferred, using additionally 1.4 mL of 40 mM sodium phosphate pH 7.4, into an iodogen-coated vial provided with a stir bar and containing IMP-R4 (0.13 μmol/100 mCi of I-131). The solution was stirred 8-15 minutes, and unincorporated radioiodine was quenched with excess of 4-hydroxyphenylacetic acid. The radioiodinated IMP-R4 was conjugated to disulfide-reduced hMN-14 (IgG-SH-to IMP-R4 ratio: 0.6 in one experiment) for 30 minutes, and unused thiol groups were capped with sodium tetrathionate. Finally, 2-3 mL of a 20% w/v suspension of anion-exchange resin AG 1X8® (100-200 mesh) in phosphate form was added and stirred for 5 minutes. The radiolabeled material was then filtered, into a sterile septum-sealed container, using Milli-Fil®GS 0.22 μm filter unit (Millipore Corporation). Human serum albumin is optionally added to the product to a final concentration of 1%-2.5%.

Typical recoveries were as follows. Starting from 57.4 mCi of I-131, the final product contained 40 mCi (69.9%), while in one run involving 123 mCi of I-131, the final product contained 63 mCi (51%). In radiolabelings (n=9) using 40 mCi-123 mCi of I-131, overall incorporations ranged 61%-75% by HPLC analyses, while the recoveries were in the 50%-70% range. Immunoreactivities, as judged by complexing with CEA and analyzing by HPLC, were >95%. The final products were >95% pure by HPLC analyses, with aggregates <5%, and with specific activities in the 5 mCi/mg-6 mCi/mg range.

Example 2

In Vitro Stability in Buffer and to Serum-Challenge

A purified product of Example-1 (62.9 mCi of total radioactivity), at a concentration of 0.9 mCi/mL and antibody concentration of 0.2 mg/mL, in phosphate buffer containing 2.5% HSA was left at the room temperature for 20 hr, and analyzed by size-exclusion HPLC. A exemplary phosphate buffer is an aqueous solution of 0.1 M sodium phosphate that is adjusted to a pH between 6.0 and 7.5. This showed that the product was practically unchanged. Complexation with 20-fold molar excess of the CEA antigen revealed the preservation of immunoreactivity.

In a second experiment, the product as above was diluted 33.3-fold in human serum, and incubated at 37° C. for 20 hr. Analysis at this time showed negligible loss of the label, and the material still complexed with CEA, indicating preservation of immunoreactivity.

Example 3

Labeling at a Lower pH, and Purification

The procedure of Example-1 was followed, with a change that buffering of I-131 sodium iodide was carried out with 7-times its volume of 0.3 M sodium phosphate pH 6, followed by transferring the buffered I-131 into iodogen vial using 1.4 mL of 0.03 M sodium phosphate, pH 6. After radioiodination, conjugation to disulfide-reduced hMN-14, and purification by stirring with AG® 1X8 anion exchange resin, a recovery of 39 mCi (69%) of purified I-131-IMP-R4-hMN-14 was obtained starting from 56.5 mCi of I-131 sodium iodide. In another experiment, using the same procedure, 69.3 mCi of purified product (63.1%) was obtained from 109.8 mCi of I-131 sodium iodide. Again, in these two experiments, complete preservation of immunoreactivity was documented using complexation with CEA.

Example 4

Radioiodination Using Immobilized Chloramine-T as Oxidant, Followed by Conjugation, and Anion-Exchange Purification In this experiment, commercially available immobilized chloramine-T (IODO-BEADS®) is used in place of iodogen. One or more beads is used in the radioiodination vial. Otherwise, the operations are identical to those described in Example-1. This way, purified I-131-IMP-R4-hMN-14 is obtained after anion-exchange purification, and isolation of product by simple filtration.

The content of any and all references, including patents, patent applications and journal articles referred to the present application is incorporated herein by reference in its entirety.

What is claimed is:

1. A method for preparing and purifying a conjugate of a radioiodinated aminopolycarboxylate-appended peptide and a targeting agent, comprising one-pot method for preparation and purification of said conjugate without a column purification step, comprising the steps of:
   (A) contacting a solution comprising;
      (i) unbound radioiodine;
      (ii) a radioiodinated aminopolycarboxylate-appended peptide (APC-peptide) that is not conjugated to a targeting agent; and
      (iii) a radioiodinated aminopolycarboxylate-appended peptide that is conjugated to the targeting agent, wherein the aminopolycarboxylate-appended peptide is selected from the group consisting of:
      X-Gly-D-Tyr-D-Lys((1-(p-CSNH)benzyl)DTPA)-OH;
      X-D-Ala-D-Tyr-D-Tyr-D-Lys(DTPA);
      [X-D-Ala-D-Tyr-D-Tyr-D-Lys(½ DTPA)]$_2$;
      X-Lys(X)-Lys((1-(p-CSNH)benzyl)DTPA)-D-Tyr-D-Tyr-D-Lys((1-(p-NH)benzyl)DTPA)-OH;
      X-Lys(X)-Lys((1-(p-CSNH)benzyl)DTPA)-D-Tyr-D-Lys((1-(p-CSNH)benzyl)DTPA)-OH;
      X-Asp-D-Tyr-D-Lys((1-(p-CSNH)benzyl)DTPA)-OH;
      X-Lys(MCC)-Asp-D-Tyr-D-Lys((1-(p-CSNH)benzyl)DTPA)-OH;
      X-Asp-D-Tyr-D-Lys-((1-(p-CSNH)benzyl)DTPA)-OH; and
      X-Lys(X)-Asp-D-Tyr-D-Lys((1-(p-CSNH)benzyl)DTPA)-OH
      wherein X is a cross-linker comprising a linking moiety that forms a covalent link with the targeting agent; with an anion exchange resin; and
   (B) filtering the solution through a filter capable of trapping anion-exchange resin particles;
   wherein the anion exchange resin binds to both unbound radioiodine and radioiodinated APC-peptide and wherein purified radioiodinated APC-peptide conjugated to targeting agent is obtained in the filtrate.

2. The method of claim 1, wherein the solution of (A) is prepared by radioiodinating an aminopolycarboxylate-appended peptide, to form a radioiodinated peptide using radioactive sodium iodide and either iodogen or immobilized chloramine-T as an oxidant; and
   conjugating the radioiodinated aminopolycarboxylate-appended peptide to a targeting agent, to form a conjugate of a radioiodinated aminopolycarboxylate-appended peptide.

3. The method of claim 2, wherein the oxidant is chloramine-T and the radioiodination is performed in the presence of immobilized, insoluble, bead form of chloramine-T.

4. The method of claim 1, wherein the filter has a pore diameter of between 0.1 μm and 0.3 μm.

5. The method of claim 1, wherein the anion-exchange resin consists of quaternary ammonium functional groups on a polymer lattice, and the extent of cross-linkage on the polymer is about 2%-12%, and the particle size of the resin is between 20 mesh-400 mesh (850 μm-38 μm particle diameter).

6. The method of claim 1. wherein the filtrate contains less than 10% of the unconjugated radioiodine and unconjugated radioiodinated peptide, combined, which were originally present in the solution prior to contacting the solution with the anion exchange resin.

7. The method according to claims 1, wherein the targeting agent is conjugated to the aminopolycarboxylate-appended peptide by a linking moiety comprising maleimide, chloroacetamide, bromoacetamide, iodoacetamide, vinylsulfone, N-hydroxysuccinimide ester, N-hydroxysulfosuccinimide ester, amidate ester, isocyanate, or isothiocyanate.

8. The method according to claim 7, wherein the maleimide linking moiety is a 4-(N-maleimidomethyl)-cyclohexane-1-carbonyl moiety.

9. The method according to claim 7, wherein the maleimide linking moiety is a 2-(N-maleimido) acetyl moiety.

10. The method of claim of 1, wherein the aminopolycarboxylate is EDTA, DTPA, benzyl-EDTA, benzyl-DTPA, benzyl-DOTA, TTHA (triethylenetetraminehexaacetic acid), NOTA, or benzyl-NOTA.

11. The method of claim 1, wherein the peptide is IMP-R4 which is:
   MCC-Lys(MCC)-Lys((1-(p-CSNH)benzyl)DTPA)-D-Tyr-D-Lys((1-(p-CSNH)benzyl)DTPA)-OH, and wherein MCC is 4-(N-maleimidomethyl)-cyclohexane-1-carbonyl moiety.

12. The method of claim of 1, wherein the targeting agent is a monoclonal antibody (MAb).

13. The method of claim 12, wherein said monoclonal antibody is an internalizing antibody.

14. The method of claim 12, wherein said monoclonal antibody is anti-CEA, MN-14; anti-EGP-1; anti-CD22; anti-CD20; anti-colon-specific antigen-p; anti-CD74; anti-MUC1; anti-AFP; anti-prostate specific membrane antigen; or anti-carbonic anhydrase IX.

15. The method of claim 12, wherein said monoclonal antibody is an intact murine, chimeric, humanized, or human antibody, or a fragment thereof.

16. The method of claim 12, wherein said monoclonal antibody is derivatized or disulfide-reduced to possess thiol groups.

17. The method of claim 1, wherein the radioiodine is I-123, I-124, I-125 or I-131.

18. The method of claim 12, wherein said monoclonal antibody is capable of targeting cardiovascular lesions, amyloid deposits, infectious organisms, inflammation, autoimmune diseases, displaced or ectopic normal tissues, or cancer.

19. The method of claim 1, wherein the targeting agent is a multivalent antibody or a multivalent, multispecific antibody.

20. The method of claim 19, wherein said multivalent antibody or multivalent, multispecific antibody binds to an antigen that is produced by or associated with an infectious organism.

21. The method of claim 19, wherein said multivalent antibody or multivalent, multispecific antibody is an internalizing antibody.

22. The method of claim 19, wherein said multivalent antibody or multivalent, multispecific antibody is derivatized or disulfide-reduced to possess thiol groups.

23. The method of claim 12, wherein said monoclonal antibody is selected from the group consisting of MN-14, RS7, LL2, 1F5, A20, Mu9, LL1, PAM-4, Immu31, J591 and G250.

* * * * *